United States Patent [19]

Ziegenhain et al.

[11] 4,254,287

[45] Mar. 3, 1981

[54] REMOVAL OF CATALYST FROM ETHOXYLATES BY CENTRIFUGATION

[75] Inventors: William C. Ziegenhain; R. Tom Jackson; LeRoy Rose, all of Ponca City, Okla.

[73] Assignee: Conoco, Inc., Ponca City, Okla.

[21] Appl. No.: 55,123

[22] Filed: Jul. 5, 1979

[51] Int. Cl.$^3$ .................. C07C 41/34; C07C 43/11
[52] U.S. Cl. ..................................... 568/621
[58] Field of Search .................. 568/621, 678, 699

[56] References Cited

U.S. PATENT DOCUMENTS

| | | | |
|---|---|---|---|
| 2,983,763 | 5/1961 | Krause | 568/621 X |
| 3,000,963 | 9/1961 | Speranza | 568/621 |
| 3,030,426 | 4/1962 | Moseley et al. | 568/621 |
| 3,328,306 | 6/1967 | Ellis | 568/678 |
| 4,129,718 | 12/1978 | Muzzio | 568/621 |
| 4,176,164 | 11/1979 | Stark | 423/116 X |

OTHER PUBLICATIONS

Merck Index (1976), Merck & Co. Inc., Rahway, N.J. p. 130.
Gilman, Organic Synthesis, vol. 1, John Wiley & Sons, New York, 1932.

*Primary Examiner*—Howard T. Mars
*Attorney, Agent, or Firm*—Cortlan R. Schupbach, Jr.

[57] ABSTRACT

Barium catalyst is removed from ethoxylated alcohols prepared using these catalysts by admixing the ethoxylated alcohols with water and mineral acid to precipitate the barium catalyst as a solid then centrifuging to remove the precipitate.

2 Claims, No Drawings

REMOVAL OF CATALYST FROM ETHOXYLATES BY CENTRIFUGATION

This invention relates to a method for removing barium catalyst from ethoxylated alcohols prepared using this catalyst. More particularly, this invention relates to a method for removing barium catalyst by mixing the ethoxylated alcohols containing said barium catalyst with particular amounts of water and mineral acid to form a precipitate, then removing this precipitate by centrifugation.

The general reaction of alcohols and ethylene oxide to form ethoxylated alcohols or ethylene oxide adducts has long been known and practiced on a commercial scale. For example, these ethylene oxide adducts have been used with detergents and cleaning agents, domestic and industrial laundry detergents, detergent builders, polishers, sanitizers and dry-cleaning materials. Other users include the pulp and paper industry and the fiber industry. These materials are especially suited to these uses since they have functional properties such as wetting power, foaming, emulsifying, and dispersing abilities as well as solubilization and detergent abilities to facilitate their use.

Ethoxylation of alcohols inevitably produces a distribution of various adducts. In some applications, an adduct with too few ethylene oxide molecules is not effective because of poor solubility, such as in surfactant applications, while an adduct with too many ethylene oxide molecules is not desirable because surface tension reduction per unit mass decreases drastically with increase in molecular weight. Thus it has long been essential to produce and use ethoxylates with a sharp distribution at a desired mole adduct range as possible. Normally, such a range is from 5 to 10. Acid catalyzed reactions produce such ethoxylates but produce harmful side products such as dioxanes which must be removed prior to use. Basic catalysts such as alkali metal hydroxides and various carbonates can also be used to catalyze this reaction. These materials form very low side products but produce undesirably broad adduct distributions.

In U.S. Application Ser. No. 916,421, filed June 16, 1978, it was disclosed that alkanols could be ethoxylated with ethylene oxide in the presence of barium hydroxide.$H_2O$ catalyst to form a low side product, sharp distribution ethoxylate which had visably improved physical properties over those adducts produced using prior art methods. However, for many uses, barium catalyst must be removed from the ethoxylated alcohol. Barium in large amounts should be used only under medical supervision. Removal of barium is therefore desirable.

It would therefore be of great benefit to provide a process whereby barium can be removed from the ethoxylated alkyl while maintaining the properties of the resulting ethoxylate.

It is therefore an object of the instant invention to provide a method for substantially complete barium catalyst removal from alkanol ethoxylates. Other objects will become apparent to those skilled in this art as the description proceeds.

It has now been found according to the instant invention that substantially all barium can be removed from ethoxylated alkanol products obtained from the barium catalyzed ethoxylation of alkanols by adding at least 130%, based upon the stoichiometric amounts of catalyst present, of a mineral acid to the ethoxylated product, adding at least 2.8 weight percent of water based on the ethoxylated product, and centrifuging until barium levels are reduced to the desired level.

The neutralization of various basic ethoxylation catalysts following by filtration to remove residues is known. Representative but not exhaustive of such art are U.S. Pat. No. 3,016,404 which in the examples shows a potassium hydroxide catalyzed reaction neutralized by hydrochloric acid to produce a precipitate, which is then removed by filtration. U.S. Pat. No. 3,030,426 shows an alkali hydroxide catalyst such as sodium, lithium, and potassium wherein stoichiometric amounts of acid are used to neutralize the catalyst and produce a precipitate, which is then removed by filtration. U.S. Pat. No. 3,393,243 shows cesium hydroxide, sodium hydroxide, and potassium hydroxide catalyst neutralized with acid and removed by filtration.

However, the barium catalysts of the instant invention are not removable by the methods of the prior art. For example, barium, when neutralized by an acid such as sulfuric acid, forms particles which aggregate like the particles of a colloid and becomes cemented together by the deposition of solid between them to form a gelatinous material. This phenomena is described by Kolthoff in *Science* volume 84, page 376 (1936). An attempt to filter such colloidal gelatinous materials results in complete plugging of the filter. Filtration procedures rapidly become inoperable.

In addition, complete removal of barium cannot be obtained by stoichiometric neutralization using a mineral acid. It has been found critical in the process of the instant invention that an excess of acid of at least 130% of stoichiometric levels be used, and that the addition of water in the amount of at least 2.8 weight percent based upon the total weight of the ethoxylate is necessary in order to remove substantially all barium from the ethoxylate as a precipitate.

Removal of the precipitate from the ethoxylate solution is best accomplished by using a centrifuge which is capable of subjecting the suspended precipitate to a separatory force of about 10,000 gravities for at least 30 seconds, or the equivalent thereof.

It has likewise been found that solution aging the neutralized barium catalyst at a temperature of about 200° F. over periods of time ranging from about 30 minutes to about 24 hours enhances crystal growth formation and facilitates catalyst removal. This phenomena is believed due to the "growth" of barium crystals as described in *Principles and Methods of Chemical Analysis,* Walton, Prentice-Hall Inc. New York, Copyright 1952 1st printing August, 52, pages 25 through 29, although this is not proven. As this reference explains, barium appears to undergo what is called an "internal Ostwald ripening" in which particles which are originally very irregular become more compact. These irregular materials dissolve at corners and edges of particles and redeposit in the particle hollows. While this fact is a contributing factor to the inability of this precipitate to be operably filtered, this fact facilitates the use of centrifugal separation.

The mineral acids useful in the product of the instant invention are those capable of forming a precipitate of barium which is insoluble in the ethoxylated alkanol. Representative examples of such acids are sulfuric, nitric, and phosphoric. Of these, sulfuric is preferred.

The acid should be added to the ethoxylated product in an amount exceeding the stoichiometric levels. Normally this amount will range from about 130 to about 300% based upon the stoichiometric amount of catalyst present. However, levels from about 140% to about 180% are preferred, and about 150% is most preferred.

Further facilitation of the separation can be accomplished by adding an excess of water ranging from about 1.5 to about 10 weight percent based upon the total ethoxylated product. However, levels ranging from about 2.8 to about 5 weight percent are preferred. Separation is carried out in either a batch or a continuous centrifuge having an equivalent separatory power of about 10,000 gravities for at least 30 seconds, or the equivalent thereof. For example, lower gravities at longer time could be used and time could be decreased using higher gravity separation. The combination of excess acid, excess water, aging and centrifugation under the conditions described can reduce barium content to levels of 10 parts per million or less, often reducing barium concentrations to less than 5 parts per million based upon the total ethoxylate product. The barium remaining in the ethoxylated product is largely present as a barium salt.

The invention is more concretely described with reference to the examples below wherein all parts and percentages are by weight unless otherwise specified. The examples are provided to illustrate the instant invention and not to limit it.

EXAMPLE 1

The ethoxylated product used in this and all subsequent experiments was prepared in a 10 gallon stainless steel autoclave. Into the autoclave were inserted 8 gallons (29.25 pounds) of ALFOL 1214 alcohol, (Trademark of and sold by Conoco Inc., 80% 12 carbon atoms and 20% 14 carbon atoms) together with 19.7 grams of barium hydroxide monohydrate catalyst. The mixture was then heated to 350° F. while mixing.

A total of 35.75 pounds of ethylene oxide was added to the autoclave over a period of several hours to produce a product containing 55 weight percent ethylene oxide. The product was then cooled from 350° F. to 200° F.

To the ethoxylated product was added a total of 571 grams of 2 weight percent sulfuric acid in deionized water. The water content in the product was thus about 1.86 weight percent. The acid addition was about 10 to 12 percent more than the theoretical amount needed to convert the barium catalyst to barium sulfate. The mixture was agitated gently for 30 minutes to insure complete contact between the acid and the catalyst and was then removed from the reactor into a closed container maintaining the 200° F. temperature. A portion of this material was withdrawn for use.

A precipitate formed in the product. Filtration was attempted using standard filtration techniques and various grades of coarse filter paper (Whatman filter paper, sizes 50 to 54). The filter paper rapidly coated with a gelatinous material which prevented passage of the liquid product.

EXAMPLE 2

Centrifugation studies were then carried out upon the material described in Example 1. The centrifuge used was a Westfalia Model SAOH-205 centrifuge capable of operating with a continuous feed and a batch discharge of the solids at operating speeds.

Operating speeds for the experiments listed was 10,600 revolutions per minute (rpm) which is equivalent to a centrifugal force of approximately 10,000 gravities. Feed rate during the experiments was 25 milliliters per minute.

Material from Example 1 was passed through the centrifuge for a period of 10 minutes and the material exiting the centrifuge was found and contained 110 parts per million barium in the product. Barium removal from the product was approximately 77%.

A second experiment was carried out wherein the accumulative run time was 40 minutes and the parts per million barium in the product recovered was about 75. The percentage barium removal was about 84%.

The desired level of barium in the finished product is 10 parts per million or less for removal of 98% or greater. Thus the stoichiometric or slight excess of acid in the prior art was not effective for the removal of barium.

EXAMPLE 3

The feedstock acid content was increased to 17.6% stoichiometric excess, in the presence of 1.84 weight percent water. Two passes through the centrifuge were made, each at 10,600 rpm. At the conclusion of the first pass the ethoxylate contained 93 ppm barium. After the second pass the centrifuged ethoxylate contained 46 ppm barium. Thus even an excess of 17.6% acid did not yield less than 10 ppm barium after two passes.

EXAMPLE 4

To 1 gallon of ethoxylate feedstock described in Example 1, an additional 38 ml of deionized water was added and thoroughly mixed into the solution. The solution was then centrifuged under operating conditions such as those described in Example 2. Run times of 10 and 40 minutes per parts per million barium in the product recovered was 16 parts per million and 12 parts per million respectively while percentage barium removal was 96.5% and 97.5%.

While these results indicate a substantial improvement when using additional water, a target of 10 parts per million barium in the finished product was not achieved. Calculated water level after the additon of water was 2.86 weight percent.

EXAMPLE 5

An additional 37 grams of 2 weight percent sulfuric acid and deionized water was added to 1 gallon of the Example 1 feedstock. This mixture was then heated to 200° F. for 30 minutes to allow uniform mixing and equilibration.

After 30 minutes, the mixture was centrifuged at 10,600 rpm in the Westfalia centrifuge at a feed rate of 75 ml per minute. After 10 and 40 minutes, the barium in the product was 35 parts per million and 3.8 parts per million for a percentage barium removal of 92.6% and 99.2 weight percent respectively.

The water level in the feed during the run was approximately 2.8 weight percent and the sulfuric acid level was about 0.218 moles sulfuric acid per 0.125 mole of barium or an excess of about 75% over the stoichiometric requirements. Higher acid levels would also be effective.

EXAMPLE 6

The reaction product of Example 1 was treated with acid and water as described in Example 5. Filtration was again attempted as shown in Example 3. Again a gelatinous material rapidly coated the filter paper and prevented further filtration.

The instant invention thus provides a method for barium removal which is efficient and can be carried out quickly. Excess added acid is not harmful to the ethoxylate product in the effective amounts used. Water is necessarily present to effectively precipitate the barium salts.

Although the process of the instant invention can be carried out as a batch reaction, it is greatly preferred to carry out as a continuous reaction as shown in the examples. The specific gravity of barium sulfate sludge as contrasted to the ethoxylated alkanol in which it was suspended is about 0.025 cc per gram heavier than the ethoxylates. In addition, the large amounts of gelatinous material formed has a specific gravity very near that of the ethoxylate product, making the gelatinous material/sludge composite with a specific gravity difference of about 0.005 to about 0.025 cc/gm heavier than the desired product. Since the sludge produced is so close to ethoxylate in specific gravity, the almost total removal of the product under the process conditions used is quite surprising.

While certain embodiments and details have been shown for the purpose of illustrating this invention, it will be apparent to those skilled in this art that various changes and modifications may be made herein without departing from the spirit or scope of the invention.

We claim:

1. A method for reducing the barium content of ethoxylated products obtained from the barium catalyzed ethoxylation of alkanols comprising
   (a) adding from about 130% to 300% based upon the stoichiometric amounts of catalyst present of sulfuric acid to ethoxylated product,
   (b) adding at least 2.8 weight percent of water and up to about 10 weight percent of water based upon the ethoxylated product and allowing the solution to age at a temperature of about 200° F. for at least 30 minutes, then
   (c) centrifuging at about 10,000 gravities for at least 30 seconds until barium levels are reduced to 10 parts per million or less in the finished ethoxylate product.

2. A method as described in claim 1 when carried out continuously.

* * * * *